US006147093A

United States Patent [19]
McCullough et al.

[11] Patent Number: 6,147,093
[45] Date of Patent: *Nov. 14, 2000

[54] METHODS FOR TREATING GASTROESOPHAGEAL REFLUX DISEASE

[75] Inventors: John R. McCullough, Hudson; Thomas P. Jerussi, Framingham, both of Mass.

[73] Assignee: Sepracor Inc., Marlborough, Mass.

[ * ] Notice: This patent is subject to a terminal disclaimer.

[21] Appl. No.: 09/123,892

[22] Filed: Jul. 28, 1998

Related U.S. Application Data

[60] Continuation-in-part of application No. 08/905,941, Aug. 5, 1997, Pat. No. 5,877,188, which is a division of application No. 08/684,753, Jul. 19, 1996, Pat. No. 5,739,151.

[51] Int. Cl.$^7$ .................................................. A61K 31/445
[52] U.S. Cl. ................................................................. 514/327
[58] Field of Search ............................................. 514/327

[56] References Cited

U.S. PATENT DOCUMENTS

| | | | |
|---|---|---|---|
| 4,962,115 | 10/1990 | Van Daele | 514/326 |
| 5,057,525 | 10/1991 | Van Daele | 514/318 |
| 5,137,896 | 8/1992 | Van Daele | 514/327 |
| 5,712,293 | 1/1998 | McCullough et al. | 514/327 |
| 5,739,151 | 4/1998 | McCullough et al. | 514/327 |

FOREIGN PATENT DOCUMENTS

| | | |
|---|---|---|
| 0 076 530 B1 | 12/1985 | Belgium . |
| WO 94/01111 | 1/1994 | WIPO . |
| WO 94/01112 | 1/1994 | WIPO . |
| WO 95/01803 | 1/1995 | WIPO . |
| WO 96/40133 | 12/1996 | WIPO . |
| WO 98/03173 | 1/1998 | WIPO . |
| WO 99/02496 | 1/1999 | WIPO . |

OTHER PUBLICATIONS

Lavrijsen, K., "A Comparative Study on the In Vitro Metabolism of Cisapride Using Subcellular Liver Fractions of Dog, Rabbit, and Male and Female Rats," *Drug Development Research*, 8:267–278 (1986).

Wong, R.H., "The Antiemetic Effects of the R– and S–Enantiomers of Cisapride and Norcisapride Against Cisplatin–Induced Emesis in the Ferret," *Society For Neuroscience Abstracts*, 23(1–2):415 (1997).

Barnes, N.M., et al, "Identification of 5–HT$_3$ Recognition Sites in the Ferret Area Postrema," *J. Pharm. Pharmacol.*, 40:586–588 (1988).

Barone, et al., "Bioavailability of Three Oral Dosage Forms of Cisapride, a Gastrointestinal Stimulant Agent," *Clinical Pharmacy*, 6:640–645 (1987).

Clarke, D.E., et al., "The 5–HT$_3$ Receptor: Naughty, but Nice," *Trends in Pharmacological Sciences*, 10:385–386 (1989).

Costall, B. et al., "Emesis Induced by Cisplatin in the Ferret as a Model for the Detection of Anti–Emetic Drugs," *Neuropharmacology*, 26:1321–1326 (1987).

Reyntjens, A., et al., "Clinical Pharmacological Evidence For Cisapride's Lack of Antidopaminergic or Direct Cholinergic Properties," *Current Therapeutic Research*, 36:5:1045–1052 (1984).

Schapira, M., et al., "The Current Status of Gastric Prokinetic Drugs," *Acta Gastroenterolog. Belg.*, LIII:446–457 (1990).

Schiavi, G.B. et al., "Identification of Serotonin 5–HT$_4$ Recognition Sites in the Porcine Caudate Nucleus by Radiogand Binding," *Neuropharmacology*, 33:543–549 (1994).

Schuurkes, J.A.J., et al., "Motor–Stimulating Properties of Cisapride on Isolated Gastrointestinal Preparations of the Guinea Pig." *J. Pharmacol. Exp. Ther.*, 234:775–783 (1985).

Stacher, G., et al., "Effects of Oral Cisapride on Interdigestive Jejunal Motor Activity, Psychomotor Function, and Side–Effect Profile in Healthy Man," *Digestive Diseases and Sciences*, 32:11:1223–1230 (1987).

Van Peer, A., et al., "Clinical Pharmacokinetics of Cisapride," Progress in the Treatment of Gastrointestinal Motility Disorders : The Role of Cisapride, Proceedings of a Symposium in Frankfurt Excerpta Medica, pp. 23–29 (1988).

Williams & Burks, "Cisapride Increases Gastric Emptying Without Affecting Small or Large Bowel Transit," *Proc. West. Pharmacol. Soc.*, 28:47–50 (1985).

Zuccato, E. et al., "The Effects of S(–) and R(+) Sulpiride, Metoclopramide, Cisapride and Doperidone on the Small Intestine Suggest DA$_2$–Receptors are involved in the Control of Small Intestinal Transit Time in Rats", *Pharmacological Research*, 26:2:179–185 (1992).

Burks, T.F., *Principles of Pharmacology*, 1996, pp. 1093–1100.

Nemeth, P.R. & Gullikson, G.W., *Chemical Abstracts*, vol. 111, No., 19, Abs. No. 167161a (1989).

Scrip's New Product Review No. 32 Cisapride, PJB Publications Ltd. (Apr. 1989).

Van Daele, G.H.P. et al., "Synthesis of Cisapride, a Gastrointestinal Stimulant Derived From Cis–4–Amino–3–Methoxypiperidine", *Drug Development Res.*, 8:225–232 (1986).

Preechagoon, Y. et al., "Analysis of Cisapride in Neonatal Plasma Using High–Performance Liquid Chromatograghy with a Base–Stable Column and Fluorescene Detection", *J. Chromatography B: Biomedical Applications*, 670(1):139–143 (1995).

(List continued on next page.)

*Primary Examiner*—William R. A. Jarvis
*Attorney, Agent, or Firm*—Pennie & Edmonds LLP

[57] ABSTRACT

Methods utilizing the optically pure (+) isomer of norcisapride are disclosed. This compound has surprisingly been found to be a potent drug for the treatment of disorders caused by gastrointestinal motility dysfunction. Finally, the (+) isomer of norcisapride also avoids certain adverse side effects and certain adverse drug interactions.

19 Claims, No Drawings

OTHER PUBLICATIONS

Craig & Clark, "5–Hydroxytryptamine and Cholinergic Mechanisms in Guinea–pig lleum," *Brit. J. Pharmacol.*, 96:247 (1989).

Decktor, D.L., et al., "Effect of Metoclopramide, Bethanechol and Cholecystokinin Receptor Antagonist, L–364, 718, on Gastric Emptying in the Rat," *Eur. J. Pharmacol.*, 147:313–316 (1988).

Dumuis, A., et al., "The Gastrointestinal Prokinetic Benzamide Derivatives are Antagonist at the Non–Classical 5–HT Receptor (5–HT$_4$) Positively Coupled to Adenylate Cyclase in Neurons," *N.S. Arch. Pharmacol.*, 340:403–410 (1989).

Fernandez & Massingham, "Peripheral Receptor Populations Involved in the Regulation of Gastrointestinal Motility and the Pharmacological Actions of Meoclopramide–like Drugs," *Life Sci.*, 36:1–14 (1985).

Frazer, A., et al., "Subtypes of Receptors for Serotonin," *Annual Rev. of Pharmacology and Toxicology*, 30:307–348 (1990).

Gladziwa, U., et al., "Pharmacokinetics and pharmacodynamics of cisapride in patients undergoing hemdialysis," *Clinical Pharmacology*, 50:6:673–681 (1991).

Gullikson, G.W., et al., "Relationship of Serotonin–3 Receptor Antagonist Activity to Gastric Empyting and Motor–Stimulating Actions of Prokinetic Drugs in Dogs," *J. Pharmacol. Experimen. Therp.*, 258(1):103–110 (1991).

Jamali, F., "Enantioselective Aspects of Drug Action and Disposition: Therapeutic Pitfalls," *Journal of Pharmaceutical Sciences*, 78(9):695–715 (1989).

Krejs, G.J., "Sérotonine intestinale, une cible thérapeutique," *Méd. Chir. Dig.*, 22:7:415–416 (1993).

Lauwers, W., et al., "Identification of a Biliary Metabolite of Cisapride," *Biomedical and Enviromental Mass Spectrometry*, 15:323–328 (1988).

Lavrijsen, K., et al., "The Role to CYP3A4 in the In–Vitro Metabolism of Cisapride in Human Liver Microsomes and In–Vitro and In–Vivo Interactions of Cisapride with Co–Administered Drugs," *Dept. of Pharmacokinetics and Drug Metabolism*, Janssen Research Foundation (1995).

Meuldermans, W., et al., "Excretion and Biotransformation of Cisapride in Dogs and Humans After Oral Administration," *Drug Metabolism and Disposition*, 16:3:403–419 (1988).

Milo, R., "Non–Cholinergic, Non–antidopaminergic Treatment of Chronic Digestive Symptoms Suggestive Of A Motility Disorder: A Two–Step Pilot Evaluation of Cisapride," *Curr. Therapeutic Research*, 36:5:1053–1062 (1984).

Nemeth, P.R., "Gastrointestinal motility stimulating drugs and 5–HT receptors or Myenteric Neurons," *Eur. J. Pharmacol.*, 166:387–391 (1989).

Porsius, A.J., et al., "Farmacotoets 6A," *Farmacotherapie*, 129:9:214–217 (1994).

METHODS FOR TREATING GASTROESOPHAGEAL REFLUX DISEASE

This application is a continuation-in-part of application Ser. No. 08/905,941, filed Aug. 5, 1997, now U.S. Pat. No. 5,877,188, which is a division of application Ser. No. 08/684,753, filed Jul. 19, 1996, now U.S. Pat. No. 5,739,151.

1. FIELD OF THE INVENTION

The present invention relates to methods and compositions for treating central nervous system ("CNS") disorders, emesis, and disorders associated with gastrointestinal motility dysfunction. In another aspect, this invention relates to metabolites of cisapride and optical isomers of such metabolites.

2. BACKGROUND OF THE INVENTION

2.1. Steric Relationship and Drug Action

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A prefix of (+) or d indicates that the compound is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Stereochemical purity is of importance in the field of pharmaceuticals, where many of the most prescribed drugs exhibit chirality. A case in point is provided by the beta-adrenergic blocking agent, propranolol, where the S-enantiomer is known to be 100 times more potent than the R-enantiomer. However, potency is not the only concern in the field of pharmaceuticals.

2.2. Pharmacologic Action

U.S. Pat. Nos. 4,962,115, 5,057,525 and 5,137,896 (collectively "Van Daele") disclose N-(3-hydroxy-4-piperidenyl)benzamides including cisapride. These compounds are said to stimulate the motility of the gastrointestinal system. Van Daele states that the cis and trans diastereomeric racemates of these compounds may be obtained separately by conventional methods, and that the cis and trans diastereomeric racemates may be further resolved into their optical isomers.

Cisapride is one of a class of compounds known as benzamide derivatives. (See: Schapira et al., *Acta Gastroenterolog. Belg.* LIII: 446–457, 1990). As a class, these benzamide derivatives have several prominent pharmacological actions. The prominent pharmacological activities of the benzamide derivatives are due to their effects on the neuronal systems which are modulated by the neurotransmitter serotonin. The role of serotonin, and thus the pharmacology of the benzamide derivatives, has been broadly implicated in a variety of conditions for many years (See Phillis, J. W., "*The Pharmacology of Synapses*", Pergamon Press, Monograph 43, 1970; Frazer, A. et al., *Annual Rev. of Pharmacology and Therapeutics* 30: 307–348, 1990). Thus, research has focused on locating the production and storage sites of serotonin as well as the location of serotonin receptors in the human body in order to determine the connection between these sites and various disease states or conditions.

In this regard, it was discovered that a major site of production and storage of serotonin is the enterochromaffin cell of the gastrointestinal mucosa. It was also discovered that serotonin has a powerful stimulating action on intestinal motility by stimulating intestinal smooth muscle, speeding intestinal transit, and decreasing absorption time, as in diarrhea. This stimulating action is also associated with nausea and vomiting.

Because of their modulation of the serotonin neuronal system in the gastrointestinal tract, many of the benzamide derivatives are often effective antiemetic agents and are commonly used to control vomiting during cancer chemotherapy or radiotherapy, especially when highly emetogenic compounds such as cisplatin are used (See: Costall et al., *Neuropharmacology* 26: 1321–1326, 1987). This action is almost certainly the result of the ability of the compounds to block the actions of serotonin (5HT) at specific sites of action, such as the 5HT3-receptor, which was classically designated in the scientific literature as the serotonin M-receptor (See: Clarke et al., *Trends in Pharmacological Sciences* 10: 385–386, 1989). Chemo- and radio-therapy may induce nausea and vomiting by the release of serotonin from damaged enterochromaffin cells in the gastrointestinal tract. Release of the neurotransmitter serotonin stimulates both afferent vagal nerve fibers (thus initiating the vomiting reflex) and serotonin receptors in the chemoreceptor trigger zone of the area postrema region of the brain. The anatomical site for this action of the benzamide derivatives, and whether such action is central (CNS), peripheral, or a combination thereof, remains unresolved (See: Barnes et al., *J. Pharm. Pharmacol.* 40: 586–588, 1988).

A second prominent action of the benzamide derivatives is in augmenting gastrointestinal smooth muscle activity from the esophagus to the proximal small bowel, thus accelerating esophageal and small intestinal transit as well as facilitating gastric emptying and increasing lower esophageal sphincter tone (See: Decktor et al., *Eur. J. Pharmacol.* 147: 313–316, 1988). Although the benzamide derivatives are not cholinergic receptor agonists per se, the aforementioned smooth muscle effects may be blocked by muscarinic receptor blocking agents such as atropine or inhibitors of neuronal transmissions such as the tetrodotoxin type which block sodium channels (See: Fernandez and Massingham, *Life Sci.* 36: 1–14, 1985). Similar blocking activity has been reported for the contractile effects of serotonin in the small intestine (See: Craig and Clarke, *Brit. J. Pharmacol.* 96: 247P, 1989). It is believed that the primary smooth muscle effects of the benzamide derivatives are the result of an agonist action upon a class of serotonin receptors referred to as 5HT4 receptors which are located on interneurons in the myenteric plexus of the gut wall (See Clarke et al., *Trends* in *Pharmacological Sciences* 10: 385–386, 1989 and Dumuis et al., *N. S. Arch. Pharmacol.* 340: 403–410, 1989). Activation of these receptors subsequently enhances the release of acetylcholine from parasympathetic nerve terminals located near surrounding smooth muscle fibers. It is the combination of acetylcholine with its receptors on smooth muscle membranes which is the actual trigger for muscle contraction.

Cisapride possesses similar properties to metoclopramide except that it lacks dopamine receptor blocking activity (See: Reyntjens et al., *Curr. Therap. Res.* 36: 1045–1046, 1984) and enhances motility in the colon as well as in the upper portions of the alimentary tract (See: Milo, *Curr. Therap. Res.* 36: 1053–1062, 1984). The colonic effects, however, may not be completely blocked by atropine and may represent, at least in part, a direct action of the drug (See: Schuurkes et al., *J. Pharmacol Exp. Ther.* 234: 775–783, 1985). Using cultured mouse embryo colliculi neurons and cAMP generation as an endpoint for designating 5HT4 activity, the EC50 concentration of racemic cisapride was $7 \times 10^{-8}$ M (See: Dumuis et al., *N. S. Arch. Pharmacol.* 340: 403–410, 1989). Drugs of this class do not affect gastric acid secretion and have variable effects upon colonic motility (See: Reyntjens et al., *Curr. Therap. Res.* 36: 1045–1046, 1984 and Milo, *Curr. Therap. Res.* 36: 1053–1062, 1984).

Racemic cisapride is used primarily to treat gastroesophageal reflux disease, which is characterized as the backward flow of the stomach contents into the esophagus. Cisapride is available only as a 1:1 racemic mixture of optical isomers, called enantiomers, i.e., a mixture of cis(−) and cis(+) cisapride known as "Prepulsid™."

The observation that cisapride enters the central nervous system and binds to 5HT4 receptors indicates that cisapride may have centrally-mediated effects. As was shown by Dumuis et al., *N. S. Arch. Pharmacol.* 340: 403–410, 1989, cisapride is a potent ligand at 5HT4 receptors, and these receptors are located in several areas of the central nervous system. Modulation of serotonergic systems may have a variety of behavioral effects.

Because of its activity as a prokinetic agent, cisapride may also be useful to treat dyspepsia, gastroparesis, constipation, postoperative ileus, and intestinal pseudo-obstruction.

Dyspepsia is a condition characterized by an impairment of the power or function of digestion that can arise as a symptom of a primary gastrointestinal dysfunction or as a complication due to other disorders such as appendicitis, gallbladder disturbances, or malnutrition. Gastroparesis is a paralysis of the stomach brought about by a motor abnormality in the stomach or as a complication of diseases such as diabetes, progressive systemic sclerosis, anorexia nervosa or myotonic dystrophy. Constipation is a condition characterized by infrequent or difficult evacuation of feces resulting from conditions such as lack of intestinal muscle tone or intestinal spasticity. Post-operative ileus is an obstruction in the intestine due to a disruption in muscle tone following surgery. Intestinal pseudo-obstruction is a condition characterized by constipation, colicky pain, and vomiting, but without evidence of physical obstruction.

The co-administration of racemic cisapride with another therapeutic agent causes inhibitory problems with the metabolism of cisapride by the liver. For example, ketoconazole has a pronounced effect on cisapride kinetics resulting from the inhibition of the metabolic elimination of cisapride and leading to an 8-fold increase in steady-state plasma levels. (See: Lavrijsen, K., et al. "The Role of CYP3A4 in the In-vitro Metabolism of Cisapride in the Human Liver Microsomes an In-vitro and In-vivo Interactions of Cisapride with Co-administered Drugs," Department of Pharmacokinetics and Drug Metabolism, Janssen Research Foundation, Beerse, Belgium). Interaction of racemic cisapride and another therapeutic agent can also potentiate cardiovascular side effects, such as cardiotoxicity. This potentiation occurs when other drugs present in the patient's system interfere with the metabolism of racemic cisapride, thereby building up racemic cisapride in the body. These interactions are a significant drawback to the use of racemic cisapride; in particular, because racemic cisapride is often used before, during or immediately after another therapeutic agent.

In addition, administration of cisapride to a human has been found to cause adverse effects including, tachycardia, central nervous system ("CNS") effects, increased systolic pressure, interactions with other drugs, diarrhea, abdominal cramping, and cardiac depression. Further, it has been reported that intravenous administration of racemic cisapride demonstrates the occurrence of additional adverse (side) effects not experienced after oral administration of racemic cisapride. (See: Stacher et al. *Digestive Diseases and Sciences* 32(11):1223–1230 (1987)).

Cisapride is almost completely absorbed after oral administration to humans, but bioavailability of the parent compound is only 40–50%, due to rapid first pass metabolism in the liver (See: Van Peer et al., in *Progress in the Treatment of Gastrointestinal Motility Disorders: The Role of Cisapride*. Proceedings of a Symposium in Frankfurt. November 1986. Johnson A. G. and Lux, G. eds. Excerpta Medica, Amsterdam, pp. 23–29 (1988)). More than 90% of a dose of cisapride is metabolized mainly by oxidative N-dealkylation at the piperidine nitrogen or by aromatic hydroxylation occurring on either the 4-fluorophenoxy or benzamide rings. It is the piperidinylbenzamide moiety of the metabolized cisapride which is identified as norcisapride. (See: Meuldermans, W. et al., *Drug Metab. Dispos.* 16(3): 410–419, 1988 and Meuldermans, W. et al., *Drug Metab. Dispos.* 16(3): 403–409, 1988). Metabolism of cisapride to norcisapride is believed to occur as follows:

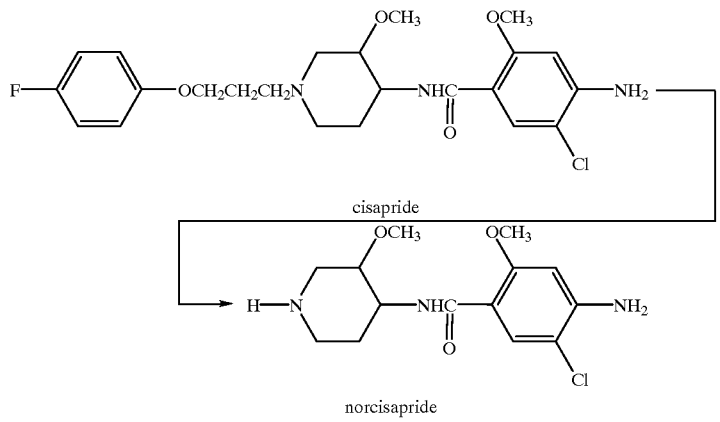

cisapride norcisapride

Norcisapride is the main urinary metabolite comprising 50–80% of the drug found in the urine of humans 72 hours after dosing. (See: Meuldermans, W. et al., *Drug Metab. Dispos.* 16(3): 410–419, 1988). Short duration of action, as seen with cisapride, can often be associated with erratic pharmacological effects following oral administration of compounds.

Thus, it would be particularly desirable to find a compound with the advantages of cisapride which would not have the aforementioned disadvantages.

3. SUMMARY OF THE INVENTION

The present invention relates to novel compositions of matter containing optically pure (+) norcisapride which are useful in treating CNS disorders. It has further been discovered that such treatment may be accomplished while substantially reducing adverse effects associated with the administration of racemic cisapride, including but not limited to diarrhea, abdominal cramping, cardiac depression and elevations of blood pressure and heart rate.

It has also been discovered that optically pure (+) norcisapride is an effective antiemetic agent, useful as an adjunctive therapy in cancer treatment to alleviate nausea and vomiting induced by chemo- or radio-therapeutics. In addition, optically pure (+) norcisapride may be used to treat emesis while substantially reducing the above-described adverse effects associated with the administration of racemic cisapride.

It has also been discovered that these novel compositions of matter containing optically pure (+) norcisapride are useful in treating gastro-esophageal reflux disease and such other conditions as may be related to the activity of (+) norcisapride as a prokinetic agent, e.g., dyspepsia, gastroparesis, constipation, post-operative ileus, and intestinal pseudo-obstruction. In addition, optically pure (+) norcisapride may be used to treat such conditions while substantially reducing the above-described adverse effects associated with the administration of racemic cisapride.

Thus, the present invention includes methods for treating the above-described conditions in a human by administering optically pure (+) norcisapride to said human. The present invention also includes methods and compositions which demonstrate an improved bioavailability over racemic cisapride irrespective of the mode of administration.

Furthermore, the present invention also includes methods and compositions for treating human disease states by having the unexpected benefit of being able to administer both optically pure (+) norcisapride and another therapeutic agent without the inhibitory effects commonly associated with the co-administration of cisapride and another therapeutic agent, e.g., adverse drug interaction.

The use of optically pure (+) norcisapride has been found to be superior to racemic cisapride or racemic norcisapride in treating the above-mentioned disease states.

4. DETAILED DESCRIPTION OF THE INVENTION

This invention relates to novel compositions of matter containing optically pure (+) norcisapride. These compositions possess activity in treating emesis. Additionally, these novel compositions of matter containing optically pure (+) norcisapride may be used to treat other conditions that may be related to the activity of (+) norcisapride as a prokinetic agent, including but not limited to dyspepsia, gastroparesis, constipation, and intestinal pseudo-obstruction. Moreover, optically pure (+) norcisapride may be used to treat these conditions while substantially reducing or avoiding adverse effects associated with the administration of racemic cisapride.

Further, the present invention encompasses the use of (+) norcisapride, substantially free of its (−) isomer, to treat central nervous system ("CNS") disorders including, e.g., but not limited to, depression, mania, bipolar affective disorder, anxiety, and panic disorder. Also disclosed are methods for treating the above-described conditions in a human while substantially reducing adverse effects that are associated with cisapride, including but not limited to diarrhea, abdominal cramping, cardiac depression, and elevations of blood pressure and heart rate, by administering the (+) isomer of norcisapride, substantially free of its (−) isomer, to a human in need of such treatment. In addition, according to the present invention, optically pure (+) norcisapride may be used to treat CNS disorders while substantially avoiding or reducing the adverse effects associated with drugs used to treat CNS disorders, e.g., such as benzodiazepines. Further disclosed are methods of treating various disease states in humans by co-administering optically pure (+) norcisapride and another therapeutic agent, while unexpectedly avoiding the adverse effects associated with administering cisapride and a therapeutic agent.

The active compound of these compositions and methods is an optically pure isomer of a metabolic derivative of cisapride, which metabolic derivative is described in Meuldermans, W. et al., *Drug Metab. Dispos.* 16(3): 410–419, 1988 and Meuldermans, W. et al., *Drug Metab. Dispos.* 16(3): 403–409, 1988.

Chemically, the active compound, of the presently disclosed compositions and methods, is the (+) isomer of the metabolic derivative of cis-4-amino-5-chloro-N-[1-[3-(4-fluorophenoxy) propyl]-3-methoxy-4-piperidinyl]-2-methoxybenzamide (hereinafter referred to as "cisapride"), known as 4-amino-5-chloro-N-(3-methoxy-4-piperidinyl)-2 methoxybenzamide hereinafter referred to as "(+) norcisapride." The term "(+) isomer of norcisapride" and particularly the term "(+) norcisapride" encompass optically pure and substantially optically pure (+) norcisapride. Similarly, as used herein, the terms "racemic cisapride", "racemic norcisapride" or "racemic mixture of cisapride" or "racemic mixture of norcisapride" refer to the cis diastereomeric racemates.

The present invention encompasses a method of treating CNS disorders in a human, and methods of treating CNS disorders in a human while substantially reducing the concomitant liability of adverse effects associated with the administration of racemic cisapride, which comprises administering to a human in need of such treatment, a therapeutically effective amount of (+) norcisapride, or a pharmaceutically acceptable salt thereof, substantially free of its (−) stereoisomer. In particular, (+) norcisapride can be used to treat a variety of CNS disorders including but not limited to (1) cognitive disorders such as Alzheimer's disease, senile dementia; (2) behavioral disorders such as schizophrenia, mania, obsessive-compulsive disorder and psychoactive substance use disorders; (3) mood disorders such as depression, bipolar affective disorder, anxiety and panic disorder; (4) disorders of control of autonomic function such as hypertension and sleep disorders; and (5) neuropsychiatric disorders, such as Gilles de la Tourette's syndrome, and Huntington's disease. These and other related disorders are well known in the art; therefore, it will be apparent to the skilled artisan based on this disclosure what other related disorders may be treated by (+) norcisapride in accordance with this invention.

In a preferred embodiment, (+) norcisapride is used to treat mood disorders, such as depression, bipolar affective disorder, anxiety and panic disorder, and behavioral disorders, such as schizophrenia, mania, and more preferably, mood disorders.

The present invention also encompasses a pharmaceutical composition for the treatment of a human suffering from a CNS disorder, which comprises a therapeutically effective amount of (+) norcisapride, or a pharmaceutically acceptable salt thereof, substantially free of its (−) stereoisomer.

The present invention further encompasses a method of eliciting an antiemetic effect in a human which comprises administering to a human in need of such antiemetic therapy, a therapeutically effective amount of (+) norcisapride, or a pharmaceutically acceptable salt thereof, substantially free of its (−) stereoisomer.

In addition, the present invention encompasses an antiemetic composition for the treatment of a human in need of antiemetic therapy, which comprises (+) norcisapride, or a pharmaceutically acceptable salt thereof, substantially free of its (−) stereoisomer.

A further aspect of the present invention includes a method of treating a condition caused by gastrointestinal motility dysfunction in a human which comprises administering to a human in need of treatment for gastrointestinal motility dysfunction, a therapeutically effective amount of (+) norcisapride, or a pharmaceutically acceptable salt thereof, substantially free of its (−) stereoisomer. Conditions caused by gastrointestinal motility dysfunction in a human include, but are not limited to, gastro-esophageal reflux disease, dyspepsia, gastroparesis, constipation, post-operative ileus, and intestinal pseudo-obstruction.

Furthermore, the present invention includes a pharmaceutical composition for treating a condition caused by gastrointestinal motility dysfunction in a human, which comprises (+) norcisapride, or a pharmaceutically acceptable salt thereof, substantially free of its (−) stereoisomer.

Further, these novel compositions may be used to treat a variety of disorders, as described above, while substantially reducing adverse effects which are caused by the administration of racemic cisapride. These novel compositions may optionally contain a pharmaceutically acceptable carrier, excipient or combinations thereof as described below.

Increased bioavailability allows for a more effective pharmacodynamic profile than racemic cisapride or racemic norcisapride and a more effective management of the disease being treated. For example, a more effective management of disorders may be achieved with the administration of (+) norcisapride, since dosing frequency can be reduced. This would facilitate, e.g., overnight treatment while the patient is asleep. Similarly, a lower dose frequency may be beneficial when (+) norcisapride is used prophylactically or as a treatment for emesis in cancer patients.

The invention also encompasses the reduction of the cardiovascular side effects which is potentiated by the co-administration of cisapride with another therapeutic agent. There can be an interaction between racemic cisapride and other therapeutic agents. For example, therapeutics which interfere with the metabolism of racemic cisapride, causing cisapride to build up in the body. This build up can cause or enhance the adverse cardiovascular effects known to be associated with racemic cisapride such as cardiotoxicity. Thus, the presence of such therapeutics either from co-administration or sequential administration before or after racemic cisapride can cause or enhance the adverse effects of racemic cisapride. The use of (+) norcisapride has unexpectedly been found to reduce these adverse side effects. It is believed that (+) norcisapride both reduces the adverse drug interactions which occur with racemic norcisapride thereby indirectly reducing adverse effects as well as reducing the adverse effects of racemic cisapride itself. Thus, (+) norcisapride can be co-administered with drugs such as ketoconazole, an agent known to inhibit the cytochrome P450 system which is responsible for the metabolism of cisapride, without causing or increasing the adverse cardiovascular side effects of racemic cisapride.

Thus, the present invention encompasses methods for treating the above described disorders in a human, which comprises administering to a human (a) a therapeutically effective amount of (+) norcisapride or a pharmaceutically acceptable salt thereof, substantially free of its (−) stereoisomer; and (b) another therapeutic agent. The inhibitory co-administration problems associated with the administration of cisapride and another therapeutic agent can be overcome by administering optically pure (+) norcisapride in conjunction with the therapeutic agent. Therefore, a physician need not be concerned about the cardiotoxic side effects of racemic cisapride when administering (+) norcisapride with another drug.

Other therapeutic agents to be used in conjunction with or which may be administered during treatment with (+) norcisapride include, but are not limited to antifungal, antiviral, antibacterial, antitumor or antihistamine agents or selective serotonin uptake inhibitors. Examples of antifungal agents include, but are not limited to ketoconazole, itraconazole and amphotericin B. Examples of antibacterial agents include, but are not limited to temafloxicin, lomefloxicin, cefadroxil and erythromycin. Examples of antiviral agents include, but are not limited to ribavirin, rifampicin, AZT, DDI, acyclovir and ganciclovir. Examples of antitumor agents include, but are not limited to doxorubicin and cisplatin. Other agents which may be co-administered with (+) norcisapride include, but are not limited to digoxin, diazepam, ethanol, acenocoumarol, fluoxetine, ranitidine, paracetamol, terfenadine, astemizole, propranolol and other agents known to inhibit the cytochrome P450 system.

Utilizing the substantially optically pure or optically pure isomer of (+) norcisapride results in clearer dose related definitions of efficacy, diminished adverse effects, and accordingly, an improved therapeutic index. Such utilization also allows the treatment of various human disease states with both optically pure (+) norcisapride and another therapeutic agent.

The term "adverse effects" includes, but is not limited to, gastrointestinal disorders such as diarrhea, abdominal cramping, and abdominal grumbling; tiredness; headache; cardiac depression; increased systolic pressure; increased heart rate; neurological and CNS effects; and adverse effects that result from the interaction of cisapride with other drugs that inhibit the metabolism of cisapride by the cytochrome P450 system including but not limited to ketoconazole, digoxin, diazepam, ethanol, acenocoumarol, cimetidine, ranitidine, paracetamol, fluoxetine, terfenadine, astemizole and propranolol.

The term "substantially free of its (−) stereoisomer" as used herein means that the compositions contain at least about 90% by weight of (+) norcisapride and about 10% by weight or less of (−) norcisapride. In a more preferred embodiment the term "substantially free of the (−) stereoisomer" means that the composition contains at least about 95% by weight of (+) norcisapride, and about 5% or less of (−) norcisapride. In a most preferred embodiment, the term "substantially free of its (−) stereoisomer" as used herein means that the composition contains about 99% by weight of (+) norcisapride. These percentages are based upon the total amount of norcisapride in the composition. The terms "substantially optically pure (+) isomer of norcisapride" or "substantially optically pure (+) norcisapride" and "optically pure (+) isomer of norcisapride" and "optically pure (+) norcisapride" are encompassed by the above-described amounts.

The terms "eliciting an antiemetic effect" and "antiemetic therapy" as used herein mean providing relief from or preventing the symptoms of nausea and vomiting induced spontaneously or associated with emetogenic cancer chemotherapy or irradiation therapy.

The term "treating a condition caused by gastrointestinal motility dysfunction" as used herein means treating the symptoms and conditions associated with this disorder which include, but are not limited to, gastro-esophageal reflux disease, dyspepsia, gastroparesis, constipation, post-operative ileus, and intestinal pseudo-obstruction.

The term "prokinetic" as used herein means the enhancement of peristalsis in, and thus the movement through the gastrointestinal tract.

The term "gastro-esophageal reflux disease" as used herein means a condition characterized by the backward flow of the stomach contents into the esophagus.

The term "dyspepsia" as used herein means a condition characterized by an impairment of the power or function of digestion that can arise as a symptom of a primary gastrointestinal dysfunction or as a complication due to other disorders such as appendicitis, gallbladder disturbances, or malnutrition.

The term "gastroparesis" as used herein means a paralysis of the stomach brought about by a motor abnormality in the stomach or as a complication of diseases such as diabetes, progressive systemic sclerosis, anorexia nervosa, or myotonic dystrophy.

The term "constipation" as used herein means a condition characterized by infrequent or difficult evacuation of feces resulting from conditions such as lack of intestinal muscle tone or intestinal spasticity.

The term "post-operative ileus" as used herein means an obstruction in the intestine due to a disruption in muscle tone following surgery.

The term "intestinal pseudo-obstruction" as used herein means a condition characterized by constipation, colicky pain, and vomiting, but without evidence of physical obstruction.

The term "co-administration" as used herein means the administration of two therapeutic agents either simultaneously, concurrently or sequentially with no specific time limits, such that both agents are present in the body at the same time.

The racemic mixture of cisapride can be synthesized by the method described in European Patent Application No. 0,076,530 A2 published Apr. 13, 1983, U.S. Pat. Nos. 4,962,115, 5,057,525 and 5,137,896 and in Van Daele et al., *Drug Development Res.* 8: 225–232 (1986), the disclosures of which are incorporated herein by reference. The metabolism of cisapride to norcisapride is described in Meuldermans, W. et al., *Drug Metab. Dispos.* 16(3): 410–419, 1988 and Meuldermans, W. et al., *Drug Metab.*

Dispos. 16(3): 403–409, 1988, the disclosures of which are incorporated herein by reference. Norcisapride can be synthesized from known commercially available starting materials in accordance with standard organic chemistry techniques. One skilled in the art can synthesize cisapride or norcisapride by the teachings of EP 0,076,530 A2 and U.S. Pat. No. 5,137,896 to Van Daele.

The (+) isomer of norcisapride may be obtained from its racemic mixture by resolution of the enantiomers using conventional means such as from an optically active resolving acid. See, for example, "Enantiomers, Racemates and Resolutions," by J. Jacques, A. Collet, and S. H. Wilen, (Wiley-Intenscience, New York, 1981); S. H. Wilen, A. Collet, and J. Jacques, Tetrahedron, 33, 2725 (1977); and "Stereochemistry of Carbon Compounds, by E. L. Eliel (McGraw-Hill, N.Y., 1962) and S. H. Wilen, page 268, in "Tables of Resolving Agents and Optical Resolutions" (E. L. Eliel, Ed. Univ. of Notre Dame Press, Notre Dame, Ind., 1972).

The magnitude of a prophylactic or therapeutic dose of (+) norcisapride in the acute or chronic management of the diseases and/or disorders described herein will vary with the severity of the condition to be treated, and the route of administration. The dose, and perhaps the dose frequency, will also vary according to the age, body weight, and response of the individual patient. Suitable dosing regimens can be readily selected by those skilled in the art with due consideration of such factors. In general, the total daily dose range for (+) norcisapride, for the conditions described herein, is from about 0.5 mg to about 500 mg, in single or divided doses. Preferably, a daily dose range should be between about 1 mg to about 250 mg, in single or divided doses, while most preferably, a daily dose range should be between about 5 mg to about 100 mg, in single or divided doses. It is preferred that the doses are administered from 1 to 4 times a day.

In managing the patient, the therapy should be initiated at a lower dose, perhaps about 5 mg to about 10 mg, and increased up to about 50 mg or higher depending on the patient's global response. it is further recommended that children, and patients over 65 years, and those with impaired renal or hepatic function, initially receive low doses, and that they be titrated based on individual response(s) and blood level(s). It may be necessary to use dosages outside these ranges in some cases as will be apparent to those skilled in the art. Further, it is noted that the clinician or treating physician will know how and when to interrupt, adjust, or terminate therapy in conjunction with individual patient response.

Any suitable route of administration may be used in order to provide the patient with an effective dosage of norcisapride. For example, oral, rectal, parenteral (subcutaneous, intramuscular, intravenous), transdermal, and like forms of administration may be employed. Dosage forms include tablets, troches, dispersions, suspensions, solutions, capsules, soft elastic gelatin capsules, patches, and the like.

The pharmaceutical compositions of the present invention comprise (+) norcisapride as the active ingredient, or a pharmaceutically acceptable salt thereof, and may also contain a pharmaceutically acceptable carrier, and optionally, other therapeutic ingredients.

The term "pharmaceutically acceptable salts" or "a pharmaceutically acceptable salt thereof" refer to salts prepared from pharmaceutically acceptable nontoxic acids or bases including inorganic acids and bases and organic acids and bases. Since the compound of the present invention is basic, salts may be prepared from pharmaceutically acceptable non-toxic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. Preferred acid addition salts are the chloride and sulfate salts. In the most preferred embodiment, (+) norcisapride is administered as the free base.

The compositions of the present invention include compositions such as suspensions, solutions and elixirs; aerosols; or carriers such as starches, sugars, microcrystalline cellulose, diluents, granulating agents, lubricants, binders, disintegrating agents, and the like, in the case of oral solid preparations (such as powders, capsules, and tablets) with the oral solid preparations being preferred over the oral liquid preparations. A preferred oral solid preparation is capsules. The most preferred oral solid preparation is tablets.

Pharmaceutical compositions of the present invention suitable for oral administration may be presented as discrete pharmaceutical unit dosage forms, such as capsules, cachets, soft elastic gelatin capsules or tablets, or aerosols sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent. Desirably, each unit dosage form, such as a tablet or soft elastic gelatin capsule, contains from about 0.5 mg to about 250 mg of the active ingredient, and preferably from about 1 mg to about 100 mg of the active ingredient, and more preferably from about 5 mg to about 50 mg. The tablet, cachet or capsule unit dosage forms may be formulated to contain one of several dosages, e.g., about 5 mg, about 10 mg, or about 25 mg of the active ingredient.

Because of their ease of administration, tablets and capsules represent the most advantageous oral dosage unit form, in which case solid pharmaceutical carriers are employed. If desired, tablets may be coated by standard aqueous or nonaqueous techniques, and may be formulated for controlled release using techniques well known in the art.

The pharmaceutical compositions of the present invention may be formulated in a soft elastic gelatin capsule unit dosage form by using conventional methods, well-known in the art (see, e.g., Ebert, *Pharm. Tech.*, 1(5):44–50 (1977)). Soft elastic gelatin capsules have a soft, globular, gelatin shell somewhat thicker than that of hard gelatin capsules, wherein a gelatin is plasticized by the addition of glycerin, sorbitol, or a similar polyol. The hardness of the capsule shell may be changed by varying the type of gelatin and the amounts of plasticizer and water. The soft gelatin shells may contain a preservative to prevent the growth of fungi, such as methyl- and propylparabens and sorbic acid. The active ingredient may be dissolved or suspended in a liquid vehicle or carrier, such as vegetable or mineral oils, glycols such as polyethylene glycol and propylene glycol, triglycerides, surfactants such as polysorbates, or a combination thereof.

In addition to the common dosage forms set out above, the compounds of the present invention may also be administered by controlled release means and/or delivery devices such as those described in U.S. Pat. Nos.: 3,845,770; 3,916,899; 3,536,809; 3,598,123; and 4,008,719, the disclosures of which are hereby incorporated by reference.

The invention is further defined by reference to the following examples, describing in detail the preparation of the compound and the compositions of the present invention, as well as their utility. It will be apparent to those skilled in the art that many modifications, both to materials and methods, may be practiced without departing from the purpose and interest of this invention.

5. EXAMPLES

5.1. Example 1

Antiemetic Effects

The relative activities of optically pure and racemic cisapride and norcisapride as antiemetic agents are determined by a pharmacological study in ferrets. Evaluation of these compounds is based on their relative potencies in a test to measure antiemesis.

Male ferrets (castrated, descented, 1.0–2.0 kg) were purchased from Triple F Farms (Sayre, Pa.). They were housed four to a cage with 12 h light cycle and fed ad libitum with Ralston Purina Cat Chow. Each ferret was used non-fasted for assay after a minimum 24 hour acclimation time in the animal facility.

Ferret Preparation. Each ferret was anesthetized with 5% isoflurane-$O_2$ mixture while placed for 2–5 min. in an anesthesia chamber. The anesthetic gas was scavenged out with an exhaust hose under vacuum. The animals were removed and weighed. Injections of study compound or vehicle were made into the dorsal front paw vein (cephalic) using a tourniquet and 1 ml tuberculin syringe with a 25 G needle while the animal was maintained under anesthesia using a small nose cone delivering 5% isoflurane-$O_2$. Each forepaw was shaved for ease of vein location. Recovery time for anesthesia was 5–8 min.

Drug Preparation. Morphine sulfate (15 mg/kg) was obtained commercially and diluted to 1 mg/ml in normal saline prior to each assay. Cisplatin bulk powder was weighed out and dissolved in normal saline heated to 75 C to make a 5 mg/ml solution (90 mg placed in scintillation vial and qs with 18 ml saline). Solution was stirred with stirring bar and kept in incubator at 40 C until injected. Solution was clear pale yellow in color. Study compound, if water soluble, was dissolved in normal saline at room temperature (10 mg base/10 ml) to make a 1 mg/ml solution as the base. For doses of 3.0 and 10.0 mg/kg, a solution of 5 mg/ml was prepared. For dose of 0.001 mg/kg a solution of 0.01 mg/ml was prepared.

Assay. Morphine emetic model: An experiment consisted of the dosing of five ferrets for each dose of study compound and one ferret as vehicle control (i.e., saline). Study compound or saline (0.5 ml) was injected i.v. at time zero. Five minutes later, morphine sulfate 0.3 mg/kg s.c. was administered in the nape of the neck. Observations were recorded over a 30 min period after morphine injection. Cisplatin model: Cisplatin 10 mg/kg was injected i.v. in each anesthetized ferret at time zero. Normal saline (0.5 ml) or study compound was injected 30 min. later in groups of six ferrets (C=1; test=5). Observations were recorded over a four hour period.

The starting dose of study compound in both assays was 1.0 mg/kg. Dosing was increased or decreased by one-half log increments. An attempt was made to test at least three doses such that percent reduction in morphine-induced emesis or cisplatin-induced emesis was 70% or greater with one dose, approximately 50% with one dose, and less than 50% with one dose. These three doses and effects were used to generate an ED 50 value.

Experimental Observations and Data Collection. A cage rack holding six ferret cages was modified with plexiglass doors and elevated cage bottoms for ease of viewing, and ferrets were placed individually in cages. Numbers of emetic episodes and retches, and times at which they occurred were recorded over a thirty minute time period starting at the time of study drug injection (morphine model). Numbers of emetic episodes and retches, and times at which they occurred were recorded over a 4 hour time period starting at the time of cisplatin injection (cisplatin model). Emetic episode was defined as an expulsion of solids or liquid, or retching resulting in mouth opening with no expulsion of stomach contents. Retches were defined as a rhythmic movement of the muscles of the rib cage. Total emetic episodes and retches were averaged for each group of five ferrets and the effect of treatment calculated as percent reduction of emetic episodes compared to control values according to the formula:

$$\frac{\text{\#episodes (saline)} - \text{\#episodes (drug)}}{\text{\#episodes (saline)}} \times 100$$

The mean % protection data points were used to generate an ED 50 value using probit analysis and RS-1 statistical package.

5.2. Example 2

Bioavailability

A single dose of test substance or vehicle is administered to male beagle dogs either intravenously as a bolus over one minute using a 23 ga butterfly needle into the saphenous vein, or as a single dose via oral gavage. 2.0 ml of whole blood is collected from each dog prior to and at intervals of 0.083, 0.25, 0.5, 1, 2, 3, 4, 6, 9, 12, and 24 hours following the intravenous or oral administration of the optical isomers or racemic mixture of cisapride or of norcisapride. The dogs are placed in sling-restraint prior to administration of test substance and are transferred to metabolic cages following collection of the 0.083 hour blood sample. All blood samples are collected from an angiocatheter placed in a cephalic vein on the morning of the experiment.

The blood is drawn into a 3 cc syringe. The first 1.0–2.0 ml of blood is discarded. The next 2.0 ml of whole blood is quickly transferred to a heparinized tube. The heparinized tubes are kept on ice until the blood is added. After adding the blood to the tube, the contents of the tube are mixed and centrifuged to obtain plasma. The plasma is carefully decanted and transferred to a test tube labelled with: the animal number, the dose of test substance administered, the route of administration, the date of administration, and the time of blood collection. The tubes are stored at −20° C. until analysis.

Analysis of the concentration of the optical isomers or racemates of norcisapride in each plasma sample is determined using high performance liquid chromatography. For each test substance the plasma concentration vs. sample time is plotted for both routes of administration. The oral bioavailability of each test substance is determined by comparing the $C_{max}$ and AUC for the oral route of administration versus those for the i.v. route. The $t_{1/2}$ for each test substance by both routes is calculated as an indicator of duration of action.

5.3. Example 3

5HT1A Receptor Activity

Receptor selection and amplification technology (R-SAT) was used (Receptor Technologies Inc., Winooski, Vt.) to determine potential agonist and/or antagonist activity of racemic norcisapride, cisapride and their enantiomers on cloned human serotonin 5-$HT_{1A}$ receptor subtypes expressed in NIH 3T3 cells (Burstein et al., *J. Biol Chem.*, 270:3141–3146 (1995); and Messier et al., *Pharmacol. Toxicol.*, 76(5):308–311 (1995)).

The assay involved co-expression of a marker enzyme, β-galactosidase, with the serotonin receptor of interest. Ligands stimulate proliferation of cells that express the receptor and, therefore, the marker. Ligand-induced effects can be determined by assay of the marker.

NIH 3T3 cells were incubated, plated, and then transfected using human 5-$HT_{1A}$ serotonin receptors, pSV-β-galactosidase, and salmon sperm DNA. The medium was changed one day later, and after 2 days, aliquots of the trypsinized cells were placed in wells of a 96 well plate. After five days in culture in the presence of the ligands, the levels of β-galactosidase were measured. The cells were then rinsed and incubated with the substrate, o-nitrophenyl β-D-galactopyranoside. After 16 hours, the plates were read at 405 nm on a plate-reader. Each compound was tested for activity in triplicate at seven different concentrations (10, 2.5, 0.625, 0.156, 0.039, 0.0098, and 0.0024 nM).

None of the compounds tested showed agonist activity at human 5-$HT_{1A}$ serotonin receptors. Data from antagonist inhibition of the compounds were fit to the equation:

$$\text{Response} = \text{Max Response} + \frac{(\text{Min Response})}{1 + (\text{Ligand Conc}/EC_{50})}$$

$IC_{50}$ values (concentration required to inhibit 50% of specific binding) were calculated for antagonist activity against a concentration of 2 μM 5-HT using the non-linear least squares analysis of KaleidaGraph, the results of which are set forth in Tables 1 and 2.

5HT2 Receptor Activity

Receptor selection and amplification technology (R-SAT) was used (Receptor Technologies Inc., Winooski, Vt.) to determine potential agonist and/or antagonist activity of racemic norcisapride, cisapride and their enantiomers on cloned human serotonin 5-$HT_2$ receptor subtypes expressed in NIH 3T3 cells (Burstein et al., *J. Biol Chem.*, 270:3141–3146 (1995); and Messier et al., *Pharmacol. Toxicol.*, 76(5):308–311 (1995)).

The assay involved co-expression of a marker enzyme, β-galactosidase, with the serotonin receptor of interest. Ligands stimulate proliferation of cells that express the receptor and, therefore, the marker. Ligand-induced effects can be determined by assay of the marker.

NIH 3T3 cells were incubated, plated, and then transfected using human 5-$HT_2$ serotonin receptors, pSV-β-galactosidase, and salmon sperm DNA. The medium was changed one day later, and after 2 days, aliquots of the trypsinized cells were placed in wells of a 96 well plate. After five days in culture in the presence of the ligands, the levels of β-galactosidase were measured. The cells were then rinsed and incubated with the substrate, o-nitrophenyl β-D-galactopyranoside. After 16 hours, the plates were read at 405 nm on a plate-reader. Each compound was tested for activity in triplicate at seven different concentrations (10, 2.5, 0.625, 0.156, 0.039, 0.0098, and 0.0024 nM). None of the compounds tested showed agonist activity at human 5-$HT_2$ serotonin receptors. Data from antagonist inhibition of the compounds were fit to the equation:

$$\text{Response} = \text{Max Response} + \frac{(\text{Min Response})}{1 + (\text{Ligand Conc}/EC_{50})}$$

$IC_{50}$ values were calculated for antagonist activity against a concentration of 2 μM 5-HT using the non-linear least squares analysis of KaleidaGraph, the results of which are set forth in Tables 1 and 2.

TABLE 1

Calculated $IC_{50}$ Values (μM) at 5-$HT_{1A}$ and 5-$HT_2$ Receptors

| Compound | 5-$HT_{1A}$ | 5-$HT_2$ |
|---|---|---|
| (±) Norcisapride | 7.48 | 2.21 |
| (+) Norcisapride | 0.0054 | 0.38 |
| (−) Norcisapride | 1.30 | — |

TABLE 2

Calculated IC$_{50}$ Values ($\mu$M) at 5-HT$_{1A}$ and 5-HT$_2$ Receptors

| Compound | 5-HT$_{1A}$ | 5-HT$_2$ |
|---|---|---|
| (±) Cisapride | — | 0.26 |
| (+) Cisapride | — | 0.0050 |
| (−) Cisapride | — | 7.08 |

5.4. Example 4

5HT3 Receptor Binding

Racemic norcisapride, racemic cisapride and their (+)- and (−)-enantiomers were tested (Cerep, Celle l'Evescault, France) for binding to 5HT$_3$ receptor subtypes derived from N1E-115 cells.

Following incubation with the appropriate ligands, the preparations were rapidly filtered under vacuum through GF/B glass fiber filters and washed with ice-cold buffer using a Brandel or Packard cell harvester. Bound radioactivity was determined with a liquid scintillation counter (LS 6000, Beckman) using a liquid scintillation cocktail (Formula 989).

Specific radioligand binding to the receptor was defined as the difference between total binding and nonspecific binding determined in the presence of an excess of unlabelled ligand. Results were expressed as a percent inhibition of specific binding obtained in the presence of the compounds. IC$_{50}$ were determined using concentrations ranging from $3\times10^{-10}$ to $10^{-5}$ M to obtain full competition curves and were calculated by non-linear regression analysis. The results are shown in Tables 3 and 4 below.

5HT4 Receptor

Racemic norcisapride, racemic cisapride and their (+)- and (−)-enantiomers were tested (Cerep, Celle l'Evescault, France) for binding to 5HT$_4$ receptor subtypes derived from guinea-pig striata.

Following incubation with the appropriate ligands, the preparations were rapidly filtered under vacuum through GF/B glass fiber filters and washed with ice-cold buffer using a Brandel or Packard cell harvester. Bound radioactivity was determined with a liquid scintillation counter (LS 6000, Beckman) using a liquid scintillation cocktail (Formula 989).

Specific radioligand binding to the receptor was defined as the difference between total binding and nonspecific binding determined in the presence of an excess of unlabelled ligand. Results were expressed as a percent inhibition of specific binding obtained in the presence of the compounds. IC$_{50}$ were determined using concentrations ranging from $3\times10^{-10}$ to $10^{-5}$ M to obtain full competition curves and were calculated by non-linear regression analysis. The results are shown in Tables 3 and 4 below.

TABLE 3

IC$_{50}$ (nM) Values for Binding to 5-HT$_3$ and 5-HT$_4$ Sites

| Compound | 5HT$_3$ | 5HT$_4$ | 5HT$_3$/5HT$_4$ Ratio |
|---|---|---|---|
| rac-Norcisapride | 8.2 | 686 | 0.012 |
| (+) Norcisapride | 4.5 | 331 | 0.014 |
| (−) Norcisapride | 30.4 | 1350 | 0.023 |

TABLE 4

IC$_{50}$ (nM) Values for Binding to 5-HT$_3$ and 5-HT$_4$ Sites

| Compound | 5HT$_3$ | 5HT$_4$ | 5HT$_3$/5HT$_4$ Ratio |
|---|---|---|---|
| rac-Cisapride | 365 | 169 | 2.2 |
| (+) Cisapride | 310 | 340 | 0.9 |
| (−) Cisapride | 2790 | 199 | 14.0 |

Agonist activity at 5HT4 receptor sites may also be assessed using an assay based on the ability of active compounds to increase cyclic AMP production in mouse embryo colloculi neurones grown in tissue culture (See: Dumuis et al., *N. S. Arch. Pharmacol.* 340: 403–410, 1989).

5.5. Example 5

Determination of Cardiovascular Effects

Unanesthetized normotensive or spontaneously hypertensive rats (SHR) are used. Blood pressure is recorded indirectly in a temperature-controlled environment before, and 1, 2, and 4 hours after, the test substance is administered by an appropriate route. The test substances are racemic, (+) and (−) cisapride and racemic, (+) and (−) norcisapride. Changes in systolic blood pressure by more than 10% (>10) at any two of the aforementioned three consecutive time points is considered significant. Tachycardia is also studied. In the same normotensive or spontaneously hypertensive rats, heart rate is recorded by a cardiograph immediately after the blood pressure recordings. An increase in heart rate greater than 20 percent (>20) from pretreatment control readings is considered significant.

Similar studies can be performed using guinea pigs or piglets.

5.6. Example 6

Central Nervous System Effects

The effects of racemic and optically pure enantiomers of norcisapride and cisapride on memory can be tested using the method described by Forster et al., *Drug Development Research*, 11:97–106 (1987). In this technique, pharmacologic effects of drugs on memory in mice are tested using a "discriminated escape" paradigm. Groups of mice are designated for vehicle and drug treatment, and each mouse is trained to enter the correct goal arm of a T-maze to escape an 0.8 mA foot shock delivered through the floor of the apparatus. The mice are dosed with vehicle or test compound during the training period.

The mice are initially given a preference trial in which entry to either goal arm will result in termination of foot shock, but they are trained to escape the shock via the arm opposite their preference in all subsequent trials. Mice are trained ("minimal training") until a learning criterion of two consecutive correct choices is met.

One week after training, all mice are tested for retention of the discrimination. The measure of retention is the percentage of correct choice trials, i.e., those in which the mouse enters the arm of the maze in which he does not receive a foot shock. Retention of discrimination is compared for the groups of mice that have been dosed, respectively, with (+) norcisapride, (−) norcisapride, racemic norcisapride, (+) cisapride, (−) cisapride, racemic cisapride and vehicle.

Effects of racemic and optically pure enantiomers of norcisapride or cisapride on sleep can be tested using electroencephalographic analysis. Groups of rats or dogs are prepared for electroencephalographic recordings by implanting cranial electrodes under general anesthesia, and then connecting these electrodes to an electroencephalic recording device after the effects of the anesthesia have worn off. These recordings are made continuously, and are used to classify the sleep state of the animal. Sleep states are classified as either "awake," "slow-wave sleep," or "REM sleep." The percentage of each of the sleep states following administration of placebo, norcisapride isomers or racemate, or cisapride isomers or racemate, is compared to evaluate the sleep-regulating effect of the tested drug.

Blockade of the conditioned avoidance response (CAR) can be used to demonstrate the ability of racemic and optically pure norcisapride or cisapride to treat the symptoms of schizophrenia. This testing procedure employs rats that are trained to avoid a foot shock by pressing a lever at the start of a test period. The start of the test period is signaled by a non-noxious stimulus (light or buzzer). Animals that are fully trained in this procedure will avoid the foot shock more than 90% of the time. Compounds that are effective antipsychotics will block this conditioned avoidance response. Thus, (−), (+), and racemic norcisapride and cisapride are tested by administering fixed doses of test and reference compounds to trained rats and then determining their relative effects on conditioned avoidance.

Racemic and optically pure cisapride and norcisapride are tested for antidepressant activity using the mouse tail suspension test (Steru et al., *Psychopharmacology* 85:367–370, 1985). A fixed dose of (−), (+) or racemic norcisapride, or (−), (+) or racemic cisapride or a reference drug is administered to a mouse, and the mouse is suspended about 15 cm above the table from a hook that is taped to the tail. The animal's movements are recorded on a polygraph. Mice typically struggle for a few minutes, and then bouts of movement are interspersed with periods of immobility ("behavioral despair"). A decrease in the total duration of immobility during a standard test session signifies potential antidepressant activity of the test compound.

Racemic and optically pure norcisapride and cisapride are tested for effects on psychoactive substance use disorders by administering test or reference compound to laboratory animals, e.g., rats, that are trained to press a lever in anticipation of receiving one of a variety of psychoactive substances ("drug self-administration"). Separate animals that have been trained to self-administer cocaine, alcohol, and morphine are employed in this study. Fixed ratios and progressive ratios are used in setting the amount of lever pressing that is required for the animal to receive the substance. (−), (+), and racemic norcisapride or cisapride are administered at fixed doses before the standard self-administration session. A decrease in the number of self-administrations or a reduction in the lever press/reward ratio indicates that the test compound has utility in treating psychoactive substance use disorders.

5.7. Example 7

| Formula | Oral Formulation Tablets Quantity per Tablet in mg. | | |
|---|---|---|---|
| | A | B | C |
| Active Ingredient (+) norcisapride | 5.0 | 10.0 | 25.0 |
| Lactose BP | 62.0 | 57.0 | 42.0 |
| Starch BP | 20.0 | 20.0 | 20.0 |
| Microcrystalline Cellulose | 10.0 | 10.0 | 10.0 |
| Hydrogenated Vegetable Oil | 1.5 | 1.5 | 1.5 |
| Polyvinylpyrrolidinone | 1.5 | 1.5 | 1.5 |
| Compression Weight | 100.0 | 100.0 | 100.0 |

The active ingredient, (+) norcisapride, is sieved through a suitable sieve and blended with the lactose until a uniform blend is formed. Suitable volumes of water are added and the powders are granulated. After drying, the granules are then screened and blended with the remaining excipients. The resulting granules are then compressed into tablets of desired shape. Tablets of other strengths may be prepared by altering the ratio of active ingredient to the excipient(s) or the compression weight.

It may be apparent to those skilled in the art that modifications and variations of the present invention are possible in light of the above disclosure. It is understood that such modifications are within the spirit and scope of the invention, which is limited and defined only by the appended claims.

What is claimed is:

1. A method of treating or preventing a disorder caused by gastrointestinal motility dysfunction in a human which comprises administering to said human a therapeutically effective amount of (+) norcisapride, or a pharmaceutically acceptable salt thereof, substantially free of its (−) stereoisomer.

2. The method of claim 1, wherein said disorder is gastro-estophageal reflux disease.

3. The method of claim 1, wherein said (+) norcisapride is administered orally.

4. The method of claim 3, wherein said (+) norcisapride is administered as a tablet.

5. The method of claim 1, wherein said (+) norcisapride is administered parenterally.

6. The method of claim 1, wherein said amount of (+) norcisapride, or a pharmaceutically acceptable salt thereof, is from about 0.5 to about 500 mg per day.

7. The method of claim 6, wherein said amount is from about 1 mg to about 250 mg per day.

8. The method of claim 7, wherein said amount is from about 5 mg to about 100 mg per day.

9. The method of claim 6, wherein said amount is administered in unit doses from one to four times a day.

10. The method of claim 1, wherein said amount of (+) norcisapride, or a pharmaceutically acceptable salt thereof, is at least about 90% by weight of the total weight of norcisapride.

11. A method of eliciting a prokinetic effect in a human to treat gastro-esophageal reflux disease in said human which comprises administering to said human a therapeutically effective amount of (+) norcisapride, or a pharmaceutically acceptable salt thereof, substantially free of its (−) stereoisomer.

12. The method of claim 11, wherein said (+) norcisapride is administered parenterally or orally as a tablet, a capsule or a liquid suspension.

13. The method of claim 12, wherein said amount of (+) norcisapride, or a pharmaceutically acceptable salt thereof, administered is from about 0.5 to about 500 mg per day.

14. The method of claim 13, wherein the amount administered is from about 1 mg to about 250 mg per day.

15. The method of claim 14, wherein the amount administered is from about 5 mg to 100 mg per day.

16. The method of claim 12, wherein said amount is administered in divided doses from one to four times per day.

17. The method of claim 11, wherein the amount of (+) norcisapride or a pharmaceutically acceptable salt thereof is at least about 90% by weight of the total weight of norcisapride.

18. The method of claim 11, wherein said (+) norcisapride or a pharmaceutically acceptable salt thereof, substantially free of its (−) stereoisomer is administered with a pharmaceutically acceptable carrier.

19. The method of claim 11, wherein said (+) norcisapride or a pharmaceutically acceptable salt thereof, substantially free of its (−) stereoisomer is administered with a pharmaceutically acceptable carrier.

* * * * *